(12) United States Patent
Quinn et al.

(10) Patent No.: US 9,354,190 B2
(45) Date of Patent: May 31, 2016

(54) APPARATUS AND METHOD FOR MONITORING AND QUANTIFYING PROGRESSION OF A STRUCTURAL ANOMALY IN A HIGH TEMPERATURE ENVIRONMENT OF A COMBUSTION TURBINE ENGINE

(71) Applicant: Siemens Energy, Inc., Orlando, FL (US)

(72) Inventors: Thomas F. Quinn, Winter Springs, FL (US); Anand A. Kulkarni, Charlotte, NC (US); James F. Landy, Cape Canaveral, FL (US)

(73) Assignee: SIEMENS ENERGY, INC., Orlando, FL (US)

( * ) Notice: Subject to any disclaimer, the term of this patent is extended or adjusted under 35 U.S.C. 154(b) by 294 days.

(21) Appl. No.: 14/164,690

(22) Filed: Jan. 27, 2014

(65) Prior Publication Data

US 2015/0212021 A1    Jul. 30, 2015

(51) Int. Cl.
| | |
|---|---|
| *G01N 25/72* | (2006.01) |
| *F01D 21/00* | (2006.01) |
| *G01M 15/14* | (2006.01) |
| *G01J 5/00* | (2006.01) |

(52) U.S. Cl.
CPC .............. *G01N 25/72* (2013.01); *F01D 21/003* (2013.01); *G01M 15/14* (2013.01); *F05D 2240/304* (2013.01); *F05D 2260/80* (2013.01); *F05D 2270/331* (2013.01); *G01J 5/0088* (2013.01); *G01J 2005/0077* (2013.01)

(58) Field of Classification Search
CPC .................................................... G01N 25/72
USPC ............................................................ 374/4
See application file for complete search history.

(56) References Cited

U.S. PATENT DOCUMENTS

| | | | |
|---|---|---|---|
| 5,184,516 A | 2/1993 | Blazic et al. | |
| 7,270,890 B2 | 9/2007 | Sabol et al. | |
| 7,432,505 B2 | 10/2008 | Brummel | |
| 7,572,524 B2 * | 8/2009 | Sabol | F01D 17/02 427/446 |
| 7,582,359 B2 * | 9/2009 | Sabol | F01D 17/02 428/469 |
| 7,618,712 B2 * | 11/2009 | Sabol | C23C 4/18 428/210 |
| 7,690,840 B2 * | 4/2010 | Zombo | F01D 5/288 250/338.1 |
| 8,004,423 B2 * | 8/2011 | Mitchell | F01D 5/288 340/573.4 |
| 8,008,932 B2 * | 8/2011 | Arndt | G01N 3/066 324/557 |
| 8,033,722 B2 * | 10/2011 | Kulkarni | F01D 5/288 374/144 |
| 8,059,008 B2 * | 11/2011 | Marincak | G01N 27/24 324/691 |
| 2011/0231110 A1 | 9/2011 | Johnston | |

* cited by examiner

*Primary Examiner* — Lisa Caputo
*Assistant Examiner* — Jamel Williams

(57) ABSTRACT

Apparatus and method for monitoring and quantifying progression of a structural anomaly, such as crack, over a surface of a component (12) in a high temperature environment of a combustion turbine engine The apparatus may include an electrically-insulating layer (14) formed at least over a portion of the surface of the component of the combustion turbine engine. At least a first detection leg (16) may be disposed on the electrically-insulating layer The first detection leg may be adapted to operate under a desired sensing modality from a bi-modal sensing scheme, such as may be implemented in one sensing modality by way of monitoring changes of an electrical parameter in an electrical circuit formed by the detection leg The sensing scheme may also be implemented by way of imaging radiance energy emitted by the detection leg.

18 Claims, 4 Drawing Sheets

APPARATUS AND METHOD FOR MONITORING AND QUANTIFYING PROGRESSION OF A STRUCTURAL ANOMALY IN A HIGH TEMPERATURE ENVIRONMENT OF A COMBUSTION TURBINE ENGINE

FIELD OF THE INVENTION

The present invention is generally related to inspection and monitoring of components, and, more particularly, to apparatus and method for monitoring and quantifying progression of a structural anomaly over a surface of a component in a high temperature environment of a combustion turbine engine

BACKGROUND OF THE INVENTION

It is known that a structural anomaly, such as a crack, that may occur in components of a combustion turbine engine, such as rotatable blades, vanes, etc., can progressively grow to a sufficiently large size which could lead to a failure event of the component, which can potentially result in costly damage and downtime of the turbine engine There is an increasing demand for real-time measurement in connection with the structural integrity of critical components in modern turbine engines, such as gas turbines, which operate at substantially high temperatures. For example, U.S. Pat. No. 7,572,524, assigned to the assignee of the present invention, describes techniques for instrumenting components in a combustion turbine engine, as may be used for collecting operational information in connection with components of the turbine engine

BRIEF DESCRIPTION OF THE DRAWINGS

The invention is explained in the following description in view of the drawings that show

DETAILED DESCRIPTION OF THE INVENTION

The present inventors have innovatively recognized certain limitations in connection with known devices for monitoring a structural anomaly as may occur in a component in a high temperature environment of a combustion turbine engine. For example, such devices may lack the ability to operate under different sensing modalities for monitoring and quantifying the progression of the structural anomaly This ability would allow performing independent cross-checks effective for validating measurements gathered in the challenging environment of a combustion turbine engine and would provide enhanced reliability in connection with the monitoring and quantifying the progression of the structural anomaly At least in view of such recognition, the present inventors propose an innovative apparatus and method for monitoring and quantifying progression of a structural anomaly over a surface of a component in a high temperature environment of a combustion turbine engine, where the apparatus may be adapted to operate under a desired sensing modality from at least a bi-modal sensing scheme available for monitoring and quantifying the progression of the structural anomaly.

Figure 1:
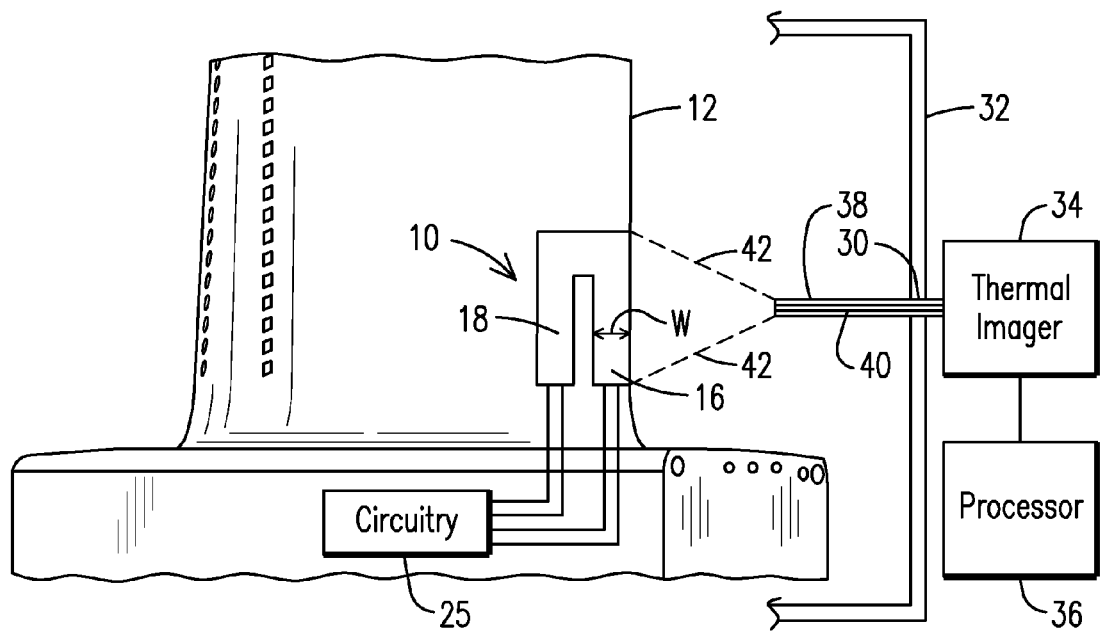
FIG. 1 is a schematic representation of one non-limiting embodiment of an apparatus for monitoring and quantifying progression of a structural anomaly over a surface of a component, such as turbine blade, a vane, etc, in a combustion turbine engine.

In the following detailed description, various specific details are set forth in order to provide a thorough understanding of such embodiments However, those skilled in the art will understand that embodiments of the present invention may be practiced without these specific details, that the present invention is not limited to the depicted embodiments, and that the present invention may be practiced in a variety of alternative embodiments In other instances, methods, procedures, and components, which would be well-understood by one skilled in the art have not been described in detail to avoid unnecessary and burdensome explanation Furthermore, various operations may be described as multiple discrete steps performed in a manner that is helpful for understanding embodiments of the present invention However, the order of description should not be construed as to imply that these operations need be performed in the order they are presented, nor that they are even order dependent unless otherwise so described. Moreover, repeated usage of the phrase "in one embodiment" does not necessarily refer to the same embodiment, although it may. Lastly, the terms "comprising", "including", "having", and the like, as used in the present application, are intended to be synonymous unless otherwise indicated FIG. 1 is a schematic representation of one non-limiting embodiment of an apparatus 10 for monitoring and quantifying progression of a structural anomaly, such as a crack, over a surface of a component 12, such as turbine blade, a vane, etc, in a combustion turbine engine.

Figure 2:
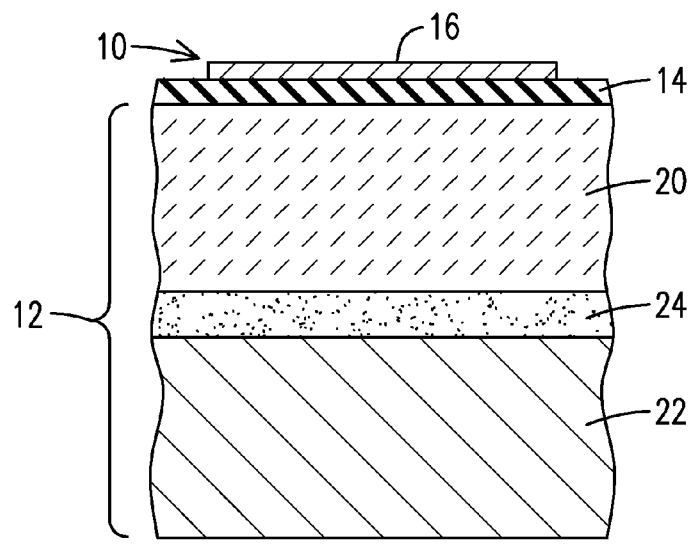
FIG. 2 is a cross-sectional view of a portion of an example turbine component including example structural details of a disclosed apparatus
Figure 3:
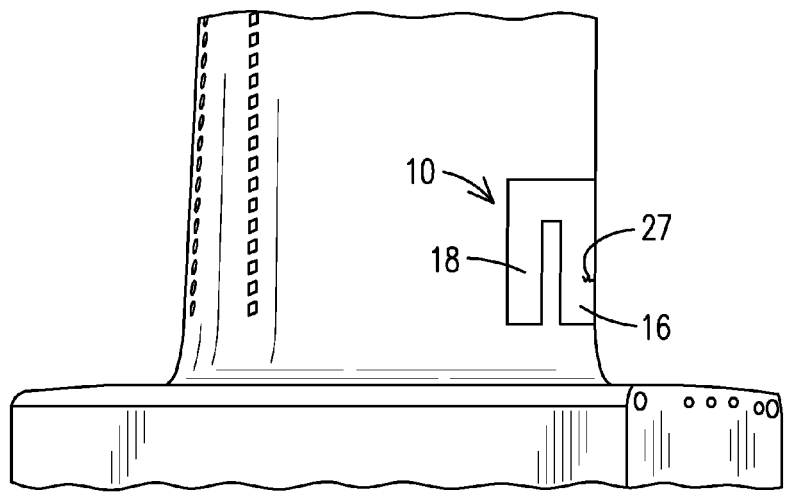
FIGS. 3-6 illustrate an example progression of crack growth as may be monitored by a disclosed apparatus
Figure 4:
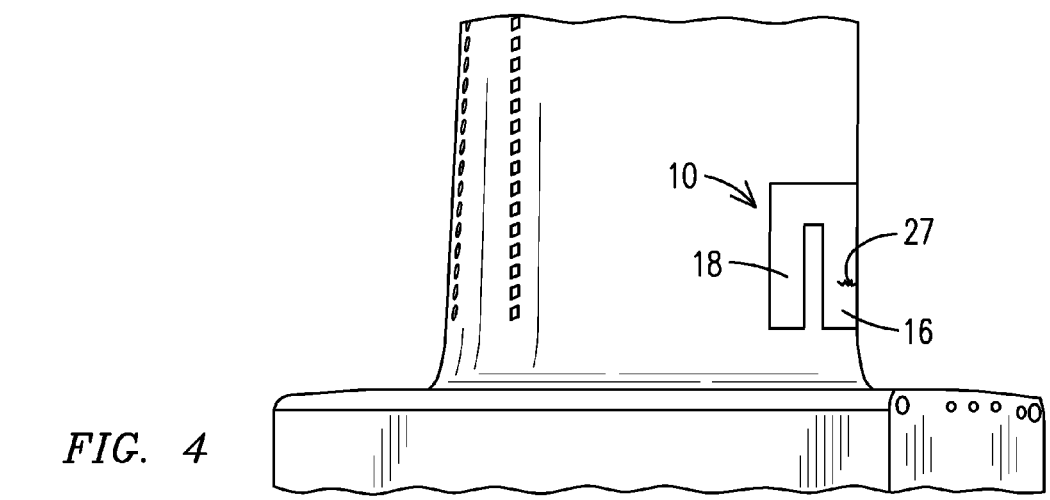
Figure 5:
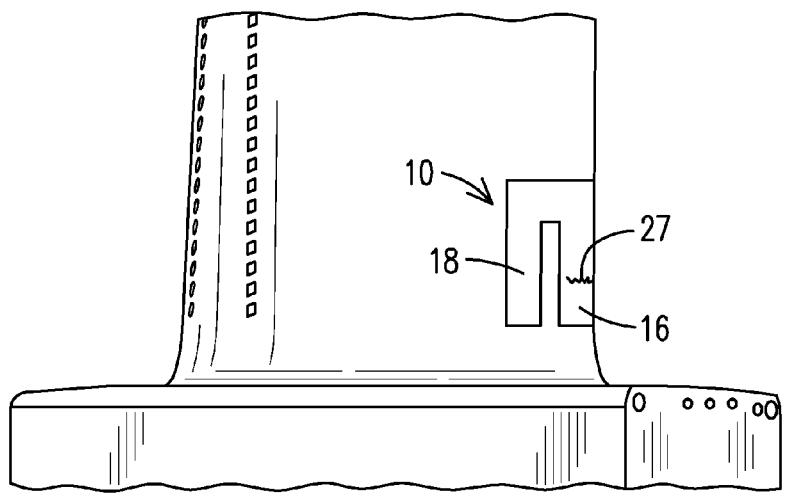
Figure 6:
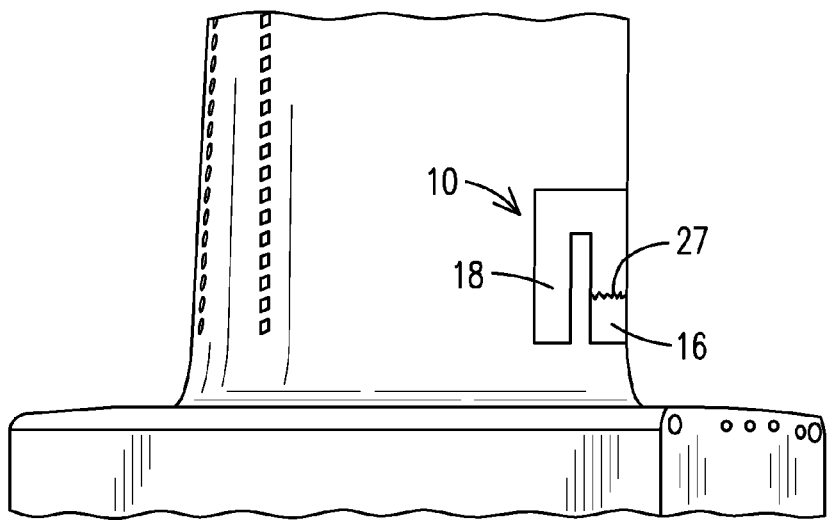

As may be appreciated in FIG. 2, in one non-limiting embodiment, turbine component 12 may comprise an underlying substrate 22 which may be bonded by way of a bond coat 24 to a thermal barrier coating (TBC) 20. As may be further appreciated in FIG. 2, in one non-limiting embodiment, apparatus 10 may comprise an electrically-insulating layer 14 formed at least over a portion of the surface of the component 12 of the combustion turbine engine, which in this example embodiment would be formed over a top surface of TBC 20.

Figure 7:
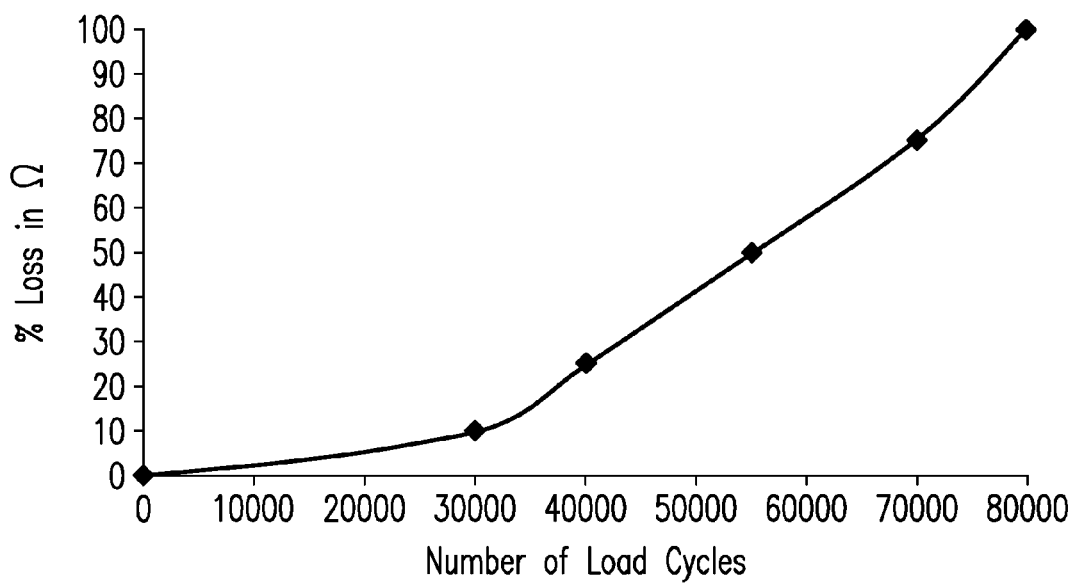
FIG. 7 is a plot of example changes in an electrical parameter, such as electrical resistance, of an electrical circuit formed by a disclosed apparatus, where such parameter changes may be plotted as a function of load cycles.

Apparatus 10 may further comprise at least a first detection leg 16 disposed on electrically-insulating layer 14 First detection leg 16 may comprise an electrically-conductive material, such as platinum or palladium metal material, or any of various austenitic nickel-chromium-based alloys, such as Inconel® alloy available from Special Metals Corporation, which have excellent chemical stability and oxidation-resistant properties and high melting point (e.g., the melting point of platinum is 1769° C.), and which can allow such detection leg to be directly exposed in the environment of a path of hot combustion gases As discussed in greater detail below, in one example embodiment, changes in an electrical parameter of an electrical circuit formed by detection leg 16 may be effectively used for monitoring and quantifying progression of the structural anomaly. Additionally, the emissivity of such example materials that may be used for forming first detection leg 16 may have a relatively high emissivity value (e.g., ranging from approximately 0 7 to approximately 0 9) at least over a wavelength range of detection (e.g., as may be utilized for thermal imaging detection) and over the high temperature range of turbine operation, which in certain embodiments may allow first detection leg 16 to additionally function as an unpowered source of radiance, such as infrared irradiance, and which may be effectively used to provide an additional sensing modality for monitoring and quantifying the progression of the structural anomaly such as by way of thermal imaging. It will be appreciated that aspects of the present invention are not limited to turbine components coated with a TBC For example, in certain applications, electrically-insulating layer 14 could be deposited on the metallic surface of a turbine component not coated with TBC In accordance with aspects of the present invention, first detection leg 16 may be operated under a desired sensing modality from a bi-modal sensing scheme that may be available for monitoring and quantifying the progression of the structural anomaly In one non-limiting embodiment, in a first sensing modality, as may be appreciated in FIG. 1, first detection leg 16 may be electrically coupled to an input leg 18 to form an electrical circuit having an electrical parameter, such as electrical resistance, indicative of the progression of the structural anomaly FIGS. 3-6 illustrate an example progression of a crack growth 27; and, as illustrated in the plot shown in FIG. 7, changes in the electrical resistance of the electrical circuit formed by detection leg 16 and input leg 18 would be indicative of the progression of crack growth, as a function of load cycles or as a function of time This information may be used for determining crack length, crack growth rate, which in turn may be used to predict a likely remaining life for the component In one example embodiment, as may be appreciated in FIG. 1, a circuitry 25 may be mounted on turbine component 12 for in-situ monitoring and wireless communication to a remote receiver (not shown) of changes in the electrical resistance indicative of the progression of the crack growth. It will be appreciated that the changes in the electrical resistance of the electrical circuit need not be monitored with in-situ circuitry For example, such monitoring may be performed by acquisition of measurements of electrical resistance by way of external test equipment that may be connected across test pads respectively connected to detection leg 16 and input leg 18 during servicing operations for the turbine.

In one example embodiment, a physical characteristic of first detection leg 16 may be chosen based on an expected characteristic of the structural anomaly For example, in the case of a crack, a width (w) of first detection leg 16 may be based on an expected characteristic of the crack, such as a predefined allowable crack size for the component. For example, the width (w) of first detection leg 16 may be chosen to approximately match the maximum allowable crack length for a given turbine component before scrapping such a component. In this example embodiment, detection of an electrical open would indicate that a given crack has reached the maximum allowable crack length for the given turbine component.

Figure 8:
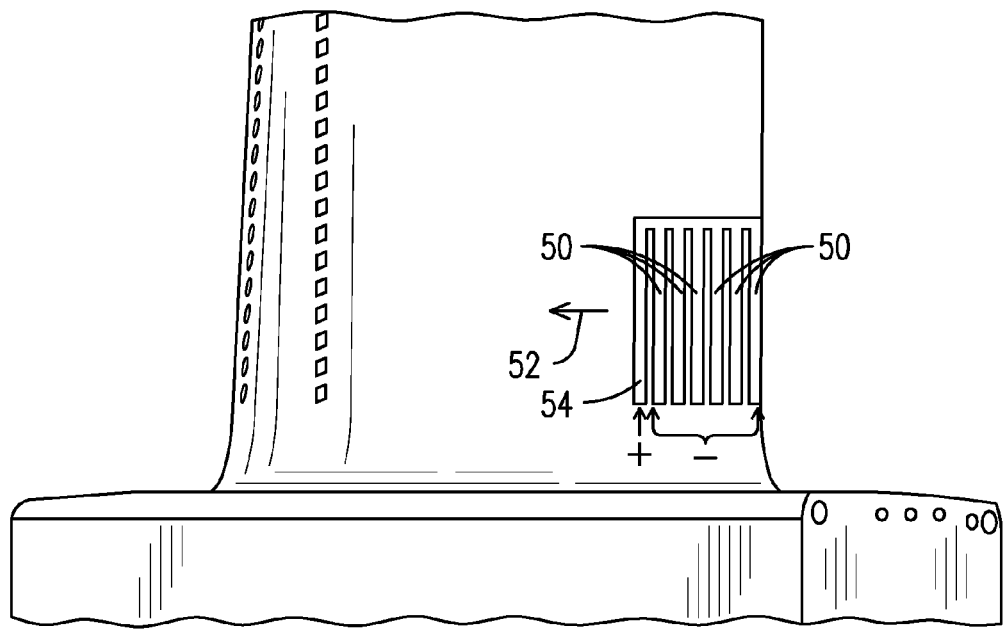
FIG. 8 is a schematic of one example embodiment of a disclosed apparatus where a plurality of detection legs may be arranged to form respective circuit loops sharing a common input leg
Figure 9:
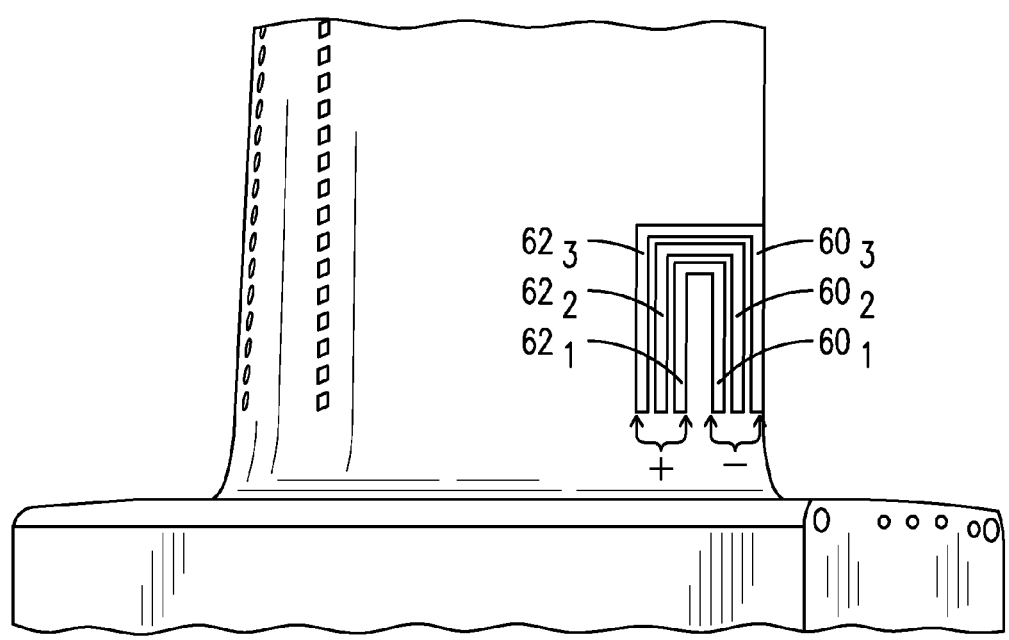
FIG. 9 is a schematic of another example embodiment of a disclosed apparatus where a plurality of detection legs may be arranged to form electrically independent circuit loops.

In one example embodiment, as may be appreciated in FIG. 8, a plurality of detection legs 50 may be arranged generally perpendicular relative to an expected direction of propagation (schematically represented by arrow 52) of the structural anomaly In one example embodiment, the plurality of detection legs 50 may be arranged to form respective circuit loops sharing a common input leg 54. For example, presuming a crack gradually propagates along the expected propagation direction, the respective circuit loops would lead to a gradual detection of respective electrical opens in correspondence with the growth of the crack In another example embodiment, as may be appreciated in FIG. 9, a plurality of detection legs, such as respective detection legs $60_1$-$60_3$ may be arranged to form electrically independent circuit loops by way of respective input legs $62_1$-$62_3$ It will be appreciated that aspects of the present invention are in no way limited to the example geometries illustrated in the drawings For example, depending on the needs of a given application, curvilinear geometries, combination of curvilinear and linear geometries may be readily implemented for the detection structures of the disclosed apparatus Accordingly, the depicted geometries should not be construed in a limiting sense In another non-limiting embodiment, in a second sensing modality as suggested above and as may be appreciated in FIG. 1, first detection leg 16 may be arranged to emit radiant energy which may be sensed through a viewing port 30 constructed in a plenum 32 by a thermal imager 34, such as an IR camera, and the sensed radiant energy may then be processed in a processor 36 to form an image indicative of the progression of the structural anomaly In one non-limiting embodiment, a viewing tube 38 may contain an optical system 40 arranged so that at least first detection leg 16 is in the field of view 42 of such optical system. Optical system 38 may be configured to provide appropriate optical conditioning (e g, focal length selection and appropriate optical magnification) to the radiant energy being received by thermal imager 34. For readers desirous of general background information regarding an example infrared (IR)-based system that can provide images of relative high spatial resolution in the context of a rotating turbine component (e g, a blade) in a turbine engine, reference is made to U.S. Pat. No. 7,690,840 titled "Method And Apparatus For Measuring On-Line Failure Of Turbine Thermal Barrier Coatings", which is herein incorporated by reference.

In operation, a disclosed apparatus for monitoring and quantifying progression of a structural anomaly provides desirable built-in redundancies in the high temperature environment of a combustion turbine engine. For example, the bi-modal sensing capability of a disclosed apparatus allows optional cross-checking of electrical-based and radiance-based measurements for monitoring and quantifying the progression of a crack in a highly challenging operational environment While various embodiments of the present invention have been shown and described herein, it will be apparent that such embodiments are provided by way of example only Numerous variations, changes and substitutions may be made without departing from the invention herein Accordingly, it is intended that the invention be limited only by the spirit and scope of the appended claims.

The invention claimed is:

1. Apparatus for monitoring and quantifying progression of a structural anomaly over a surface of a component in a high temperature environment of a combustion turbine engine, the apparatus comprising an electrically-insulating layer formed at least over a portion of the surface of the component of said combustion turbine engine; and at least a first detection leg disposed on the electrically-insulating layer, wherein the first detection leg is configured to operate under a desired sensing modality from a bi-modal sensing scheme available for monitoring and quantifying the progression of the structural anomaly.

2. The apparatus of claim 1, wherein said at least first detection leg comprises an electrically-conductive material selected from platinum, palladium and a nickel-chromium-based alloy.

3. The apparatus of claim 2, wherein in a first sensing modality said at least first detection leg is electrically coupled to form an electrical circuit having an electrical parameter indicative of the progression of the structural anomaly.

4. The apparatus of claim 3, wherein a physical characteristic of said at least first detection leg is chosen based on an expected characteristic of the structural anomaly.

5. The apparatus of claim 4, wherein the structural anomaly comprises a crack, and wherein the chosen physical characteristic of said at least first detection leg is a width of said at least first detection leg.

6. The apparatus of claim 5, wherein the width of said at least first detection is chosen based on a predefined allowable crack size for the component.

7. The apparatus of claim 2, comprising a plurality of detection legs arranged generally perpendicular relative to an expected direction of propagation of the structural anomaly, wherein the plurality of detection legs are arranged to form respective circuit loops sharing a common input leg.

8. The apparatus of claim 2, comprising a plurality of detection legs arranged generally perpendicular relative to an expected direction of propagation of the structural anomaly, wherein the plurality of detection legs are arranged to form electrically independent circuit loops.

9. The apparatus of claim 2, wherein in a second sensing modality said at least first detection leg is arranged to emit radiant energy which is sensed by a thermal imager and the sensed radiant energy is processed in a processor to form an image indicative of the progression of the structural anomaly.

10. A method for monitoring and quantifying growth of a structural anomaly over a surface of a component of a high temperature environment of a combustion turbine engine, the method comprising forming an electrically-insulating layer at least over a portion of the surface of the component of said combustion turbine engine; disposing at least a first detection leg on the electrically-insulating layer; and operating said at least first detection leg under a desired sensing modality from a bi-modal sensing scheme available for monitoring and quantifying the progression of the structural anomaly.

11. The method of claim 10, wherein said at least first detection leg comprises an electrically-conductive material selected from platinum, palladium and a nickel-chromium-based alloy.

12. The method of claim 11, wherein in a first sensing modality, further comprising electrically coupling said at least first detection leg to form an electrical circuit having an electrical parameter indicative of the progression of the structural anomaly.

13. The method of claim 12, further comprising monitoring changes in the electrical parameter to determine the progression of the structural anomaly.

14. The method of claim 10, wherein the structural anomaly comprises a crack, and further comprising choosing a width of said at least first detection leg based on an expected characteristic of the crack.

15. The method of claim 14, wherein the choosing of the width of said at least first detection leg is based on a predefined allowable crack size for the component.

16. The method of claim 11, further comprising arranging a plurality of detection legs generally perpendicular relative to an expected direction of propagation of the structural anomaly, and forming with the plurality of detection legs circuit loops sharing a common input leg.

17. The method of claim 11, further comprising arranging a plurality of detection legs generally perpendicular relative to an expected direction of propagation of the structural anomaly, and forming with the plurality of detection legs electrically independent circuit loops.

18. The method of claim 11, wherein in a second sensing modality, further comprising sensing radiant energy emitted by said at least first detection leg and processing the sensed radiant energy to form an image indicative of the progression of the structural anomaly.

\* \* \* \* \*